(12) United States Patent
Keri et al.

(10) Patent No.: US 6,858,414 B2
(45) Date of Patent: Feb. 22, 2005

(54) MULTISTAGE PROCESS FOR THE PREPARATION OF HIGHLY PURE DEFEROXAMINE MESYLATE SALT

(75) Inventors: Vilmos Keri, Debrecen (HU); Zoltan Czovek, Debrecen (HU); Attila Mezo, Debrecen (HU)

(73) Assignee: Biogal Gyógyszergyár Rt., Debrecen (HU)

( * ) Notice: Subject to any disclaimer, the term of this patent is extended or adjusted under 35 U.S.C. 154(b) by 2 days.

(21) Appl. No.: 10/168,042

(22) PCT Filed: Nov. 30, 2000

(86) PCT No.: PCT/US00/32574

§ 371 (c)(1),
(2), (4) Date: Jun. 18, 2002

(87) PCT Pub. No.: WO01/40164

PCT Pub. Date: Jun. 7, 2001

(65) Prior Publication Data

US 2003/0059905 A1 Mar. 27, 2003

(30) Foreign Application Priority Data

Dec. 1, 1999 (HU) ............................................ 9904454

(51) Int. Cl.⁷ .......................... C12P 13/02; C12P 13/00; C07C 259/04; C07C 309/00; B01D 15/08
(52) U.S. Cl. ..................... 435/129; 435/128; 435/243; 435/247; 562/114; 562/623; 560/159
(58) Field of Search ................................ 435/128, 129, 435/243, 247; 562/114, 623

(56) References Cited

U.S. PATENT DOCUMENTS

| | | | |
|---|---|---|---|
| 3,118,823 A | * 1/1964 | Gaeumann et al. | 435/121 |
| 3,153,621 A |   10/1964 | Gaeumann et al. | 435/128 |
| 3,247,197 A |    4/1966 | Gaeumann et al. | 562/623 |
| 4,987,253 A | * 1/1991 | Bergeron | 562/623 |
| 5,254,724 A |   10/1993 | Bergeron et al. | 562/623 |
| 5,322,961 A | * 6/1994 | Bergeron, Jr. | 562/623 |
| 5,364,965 A | * 11/1994 | Bergeron, Jr. | 562/623 |
| 5,367,113 A | * 11/1994 | Bergeron, Jr. | 562/623 |
| 5,374,771 A |   12/1994 | Koyari et al. | 562/623 |
| 5,430,176 A | * 7/1995 | Wuts | 560/159 |
| 5,493,053 A | * 2/1996 | Bergeron, Jr. | 562/623 |

FOREIGN PATENT DOCUMENTS

| | | |
|---|---|---|
| EP | 0 347 163 | 12/1989 |
| WO | WO 93/03045 | 2/1993 |
| WO | 93/09088 | 5/1993 |

OTHER PUBLICATIONS

Goodman & Gilman's The Pharmacological Basis of Therapeutics, 9$^{th}$ Ed. (1996) "Deferoxamine", pp. 1668–1669, The McGraw–Hill Companies.

Physicians' Desk Reference, 53$^{rd}$ Ed. (1999) "Desferal®", pp. 2010–2011, Medical Economics Company, Inc.

Bickel, H. et al., "Stoffwechselprodukte von Actinomyceten" Helvetica Chimica Acta, vol. XLIII, No. 261, (1960) pp. 2129–2138.

The United States Pharmacopeia/The National Formulary USP24/NF19 (1999), "Deferoxamine Mesylate" pp. 499–200, United States Pharmacopeial Convention, Inc.

The United States Pharmacopeia/The National Formulary USP24/NF19 (1999), "<221> Chloride and Sulfate" pp. 1857–1858, United States Pharmacopeial Convention, Inc.

The United States Pharmacopeia/The National Formulary USP24/NF19 (1999), "<921> Water Determination" pp. 2003–2004, United States Pharmacopeial Convention, Inc.

* cited by examiner

*Primary Examiner*—Herbert J. Lilling
(74) *Attorney, Agent, or Firm*—Kenyon & Kenyon

(57) ABSTRACT

The present invention provides a purification process whereby deferoxamine B produced by a microorganism and in mixture with other polyhydroxamates produced by the microorganism may be converted into its mesylate salt substantially free of the other polyhydroxamates and substantially free of chloride ion. The process includes adsorption and desorption of the deferoxamine B on an adsorption resin, direct precipitation of the deferoxamine free base out of the eluent from the adsorption resin, contacting of the deferoxamine B free base with methanesulfonic acid and isolation of the deferoxamine B mesylate salt by precipitation. This process minimizes decomposition of deferoxamine B.

26 Claims, No Drawings

MULTISTAGE PROCESS FOR THE PREPARATION OF HIGHLY PURE DEFEROXAMINE MESYLATE SALT

RELATED APPLICATION

This application claims the benefit under 35 U.S.C. §119 of Hungarian Patent Application P 99 04454, filed Dec. 1, 1999.

FIELD OF THE INVENTION

This invention relates to a process for preparing highly pure deferoxamine B mesylate.

BACKGROUND OF THE INVENTION

Deferoxamine B, represented by formula I, is a polyhydroxamate iron chelator that is useful for reducing iron concentration in human blood plasma.

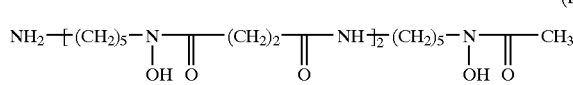

(I)

The systematic chemical name of deferoxamine B (also known as deferriferrioxamine B) is N'-[5-[[4-[[5-(acetylhydroxyamino)pentyl]amino]-1,4-dioxobutyl]hydroxyamino]pentyl]-N-(5-aminopentyl)-N-hydroxy-butanediamide. Deferoxamine B has the desirable property of high affinity for ferric iron ($Ka=10^{31}$) coupled with a very low affinity for calcium ($Ka=10^2$). Goodman and Gilman, *The Pharmacological Basis of Therapeutics* 1668 (9th ed. 1996).

Deferoxamine B is indicated for treatment of acute iron intoxication and chronic iron overload due to transfusion dependant anemias. It promotes iron excretion in patients with secondary iron overload from multiple transfusions, as may occur with treatment of some chronic anemias such as thalassemia. Long term therapy slows accumulation of hepatic iron and retards or eliminates progression of hepatic fibrosis. *Physicians Desk Reference* 2010 (54th ed. 1999). Deferoxamine B is not well-absorbed orally; it must be administered parenterally.

Industrial scale fermentation processes for producing deferoxamine B use the *Streptomyces pilosus* bacteria strain, which produces a variety of polyhydroxamate compounds, but predominantly deferoxamine B, in a culture medium poor in iron. Belgian Patent No. 619,532. Deferoxamine B is typically isolated from the fermentation broth as its hydrochloride salt. The hydrochloride salt is not pharmaceutically acceptable for parenteral administration to humans. Therefore, it must be converted into a pharmaceutically acceptable salt. The mesylate salt is the FDA approved deferoxamine salt. The *U.S. Pharmacopeia & National Formulary* directs that pharmaceutical grade deferoxamine B mesylate contain not more than 120 ppm chloride. *USP/NF* 24/19, pp. 499–500 (1999). This has proven to be a challenging standard to meet and there remains a need for an improved process for transforming deferoxamine B produced by fermentation into a pharmaceutically acceptable pure mesylate salt for administration to patients.

Belgian patent 619,532 discloses purification of deferoxamine B obtained via fermentation using adsorption chromatography. Activated carbon, activated diatomaceous earth (e.g. fuller's earth) or ion-exchange resin (Asmit) are recommended adsorbents. Alternative adsorbents are said to include aluminum oxide, magnesium silicates, silica gel, gypsum and ion-exchange resins. According to the Belgian 619,532 patent, deferoxamine B may be eluted using a mobile phase of methanol-water, pyridine-water or acetic acid-methanol.

International Publication No. WO 93/09088 and European patent 347,163 describe chromatography over silica gel as a method for purifying deferoxamine B produced by synthetic means, not by microbiological means.

International Publication No. WO 93/03045 describes purification of iron chelate complexes of deferoxamine B and structurally related compounds using a polystyrene adsorption resin.

U.S. Pat. Nos. 3,153,621 and 3,118,823 disclose partial purification of deferoxamine B using ion-exchange resins. It is believed that the teachings of these patents lead to a mixture of deferoxamine B with other polyhydroxamates that are produced by the *Streptomyces pilosus* strain.

Belgian Patent 616,139 discloses that deferoxamine B mesylate salt can be obtained from the deferoxamine B hydrochloride salt by passing an aqueous solution of deferoxamine hydrochloride over Dowex-1, X-16 anion exchange resin (in OH⁻ form), adding methanesulfonic acid in equivalent quantity to the resulting deferoxamine base in aqueous solution, then evaporating the water and, lastly, purifying the deferoxamine mesylate salt by recrystallization from aqueous alcohol or a mixture of water-methanol-acetone.

U.S. Pat. No. 5,374,771 describes purification of crude deferoxamine B hydrochloride by ion-exchange chromatography and multiple recrystallizations. The mesylate salt is prepared directly from the purified deferoxamine B hydrochloride by contacting with an anion exchange resin having mesylate counter-ion. Deferoxamine B mesylate is obtained from the aqueous solution by lyophilization.

Bickel, H. et al., *Helvetica Chimica Acta*, 1385–1389 (1963), describes purification of deferoxamine B base by multiple recrystallizations from a water-alcohol mixture. The deferoxamine B base is prepared by anion exchange, evaporation to dryness, and multiple recrystallizations. The deferoxamine B base is then suspended in a water-methanol mixture and a mineral acid salt prepared. Subsequently the deferoxamine B solution is evaporated and the residue is recrystallized from a water-methanol mixture.

Removal of chloride ion from an aqueous solution of deferoxamine B is one of the steps in each of the methods described above for purifying deferoxamine B from a fermentation broth. In each case, the chloride ion is removed using an anion exchange resin. However, ion-exchange resins alone are not effective for isolating deferoxamine B mesylate free of chloride ion as is required in order to achieve a pharmaceutically acceptable state of purity.

The above-mentioned purification methods that use silica gel or aluminum oxide as adsorbents are inefficient, time consuming and expensive. The other conventional substitutes—activated charcoal, diatomaceous earth, magnesium silicates, and gypsum—are poor adsorbents of deferoxamine. For these reasons, there remains a need in the art for a rapid, efficient and inexpensive method for obtaining deferoxamine B mesylate from a fermentation broth free of chloride ion, or at least free of chloride anion in an amount greater than 120 ppm.

Furthermore, the above-described methods do not efficiently remove fermentation products that are structurally related to deferoxamine B, which must be removed before use of the deferoxamine B in a pharmaceutical product. Typically, an extract from a deferoxamine-producing fermentation broth contains, relative to the deferoxamine B content, approximately 6 to 20 mole % polyhydroxamate compounds that are structurally related to deferoxamine B. Such compounds include other deferoxamines, such as deferoxamine A, C, $D_1$, $D_2$, E, F and G. Since deferoxamine B and the other deferoxamines have similar chemical properties, none of the known purification processes or combinations thereof have been able to reduce the quantity of the impurities below about 2.5%.

In addition to their uncertain therapeutic, and possibly toxic effect it is important to remove these impurities in order to accurately determine the deferoxamine B concentration in a solution, such as a sterile solution for injection. The *USP/NF* specifies that a deferoxamine B injection solution contain between 90.0 and 110% of the labeled concentration. *USP/NF* 24/19, p. 500 (1999) The assay for determining concentration specified by the *USP/NF* is a photometric absorbence intensity measurement of the iron complex at 485 nm. Id. The structurally related impurities also form complexes which absorb in the 485 nm range, leading to an overestimation of the deferoxamine B content. We have found that a photometric assay of a solution of deferoxamine B mesylate obtained by fermentation according to methods known in the art overestimates the concentration of deferoxamine B by about 3%. Thus, there remains a need in the art for a rapid, efficient and inexpensive method for obtaining deferoxamine B mesylate from a fermentation broth free of other polyhydroxamates formed by the metabolic processes of *Streptomyces* (e.g. *pilosus* or 101/87) as well as free of chloride ion.

SUMMARY OF THE INVENTION

The need for high purity in drugs in order to prevent undesirable effects caused by impurities and the need for accuracy in determining the potency of a deferoxamine B mesylate drug are both met by the present invention. In the course of our experiments with deferoxamine B, we found that fermentation byproducts that are chemically unrelated to deferoxamine B and related substances with significantly different polarity could be removed by adsorption chromatography, but that other polyhydroxamates could not. We have found that the most effective means of reducing the quantity of other polyhydroxamates is by precipitation of the deferoxamine B free base after preliminary cleanup by adsorption chromatography. We also found that decomposition products are formed if deferoxamine B is evaporated to dryness. Deferoxamine B is a reasonably stable solid, but it is prone to decomposition in concentrated solution. As a dilute solution of deferoxamine B is evaporated, the solution concentration rises, which causes decomposition and a solidified product of low purity. We found that this decomposition can be minimized by concentration- and pH-adjustment of the eluent from the adsorption resin within certain parameters and then direct precipitation of deferoxamine B free base from the eluent.

Thus, we have discovered that in order to efficiently remove both chloride and polyhydroxamate impurities, to minimize the formation of decomposition products, and to separate them to the extent that their formation is unavoidable, that one should apply, in succession, chromatography on adsorption resin, precipitation of the deferoxamine B free base from a mixture of water and a water-soluble organic solvent, formation of the deferoxamine mesylate salt and crystallization of that salt from a mixture of water and a mesylate salt anti-solvent or from a mixture of methanol and a mesylate salt anti-solvent. This process produces deferoxamine B mesylate containing less than 2.5 mole % of other polyhydroxamate impurities and less than 90 ppm chloride ion.

DETAILED DESCRIPTION OF THE INVENTION

The present invention provides a purification process for production of highly pure deferoxamine B mesylate from a source material containing deferoxamine B produced by a microbiological process. The purification process is feasible on an industrial scale and is highly economical compared to other known purification processes.

Microbiological processes for producing deferoxamine B are known in the art, such as the method described in U.S. Pat. No. 3,158,552, which is herein incorporated by reference in its entirety. As described in the '552 patent, *Streptomyces pilosus* is cultivated in a submersion medium with a low iron content to stimulate production of deferoxamines which the microorganism uses to extract iron from its environment. At the end of the fermentation, deferoxamine B is freed from complexation with $Fe^{3+}$ ions in the culture medium by addition of a competitive iron chelating agent, 8-hydroxyquinoline. The broth is then filtered to remove cell mass and an aqueous solution containing deferoxamine B is obtained. After further processing, deferoxamine B hydrochloride, in mixture with other deferoxamines, is precipitated from aqueous solution.

The process of the present invention may be applied to a source material obtained from a fermentation broth after processing such as concentration or extraction as described in the '552 patent or after processing as described in U.S. Pat. No. 5,374,771. Likewise, an evaporated fermentation broth extract containing deferoxamine B may be taken up in either aqueous or organic solvent and used as source material for deferoxamine B. Preferably, the source material of deferoxamine B is an aqueous solution with a deferoxamine B concentration of from about 5 to about 70 g $L^{-1}$, more preferably from about 10 to about 30 g $L^{-1}$. The purification process is further described as it is applied to such an aqueous solution of deferoxamine B (hereafter "the crude deferoxamine B solution").

The purification process of the present invention comprises three stages. First, impurities chemically unrelated to deferoxamine B and related substances with significantly different polarity are removed by chromatography over an adsorption resin. In the second stage, deferoxamine B is separated from chloride anion and other polyhydroxamates by precipitation of the deferoxamine B as its free base. In the third stage, the deferoxamine B, in free base form, is suspended in a mixed solvent, treated with methanesulfonic acid to dissolve the free base and crystallized as its mesylate salt.

Chromatographic Separation of Impurities

In the first stage of the invention, compounds that are chemically dissimilar to deferoxamine B and related substances with significantly different polarity are substantially separated by contacting the deferoxamine B source material with a bed of adsorption resin and collecting deferoxamine B in solution as an eluent from the bed. Preferred adsorption resins are unsubstituted and substituted aromatic type resins, aromatic resins with hydrophobic groups, acrylic and methacrylic resins. Especially preferred adsorption resins include Diaion® resins of the FP, HP, SP and HPMG series (Mitsubishi Chemical Corp.) and Amberlite® resins of the XAD series (Rohm & Haas), the most preferred being Diaion® SP 207 and Amberlite® XAD 1180. Deferoxamine B can be eluted from these resins with a mixture of water and a water-soluble organic solvent such as methanol, ethanol, acetonitrile and tetrahydrofuran.

A preferred chromatographic procedure uses a pre-column and a main column containing separate beds of adsorption resin. According to this preferred procedure, the crude deferoxamine B solution is first eluted through the pre-column which contains a small amount of adsorption resin, i.e. about 2 to 6 one hundredths of the volume of the crude deferoxamine B solution. The pre-column may be mounted atop the main column and the crude deferoxamine B solution may be allowed to pass through the pre-column without eluting with solvent because only a minor portion of the deferoxamine B is adsorbed on the pre-column. Alternatively, the pre-column may be eluted with solvent. The eluent may be a mixture of water and a water-soluble organic solvent as described above, but preferably, for improved retention of deferoxamine B on the main column, the elution solvent, if used, is salt water as described below. A pre-column may result in a small reduction in yield of deferoxamine B mesylate at the end of the process but its use has the advantage of higher ultimate purity and the economic advantage of greater ease of regeneration of the adsorption resin of the main column.

After optionally passing the crude deferoxamine B solution through a pre-column, the solution is preferably treated with an inorganic salt to enhance adsorption of deferoxamine B on the main column. Chloride salts and sulfate salts are preferred inorganic salts, the most preferred being ammonium chloride and ammonium sulfate. The inorganic salt should be added in amount of about 2 to about 15 g $L^{-1}$ of solution, more preferably about 5–10 g $L^{-1}$. The crude deferoxamine B solution is then loaded onto a main column containing a bed of absorption resin whose volume is from about ½oth the volume of the crude deferoxamine B solution to about the same volume as that of the crude deferoxamine B solution. Preferably, the volume of the bed of absorption resin is from about ¼ to about ¾ the volume of the crude deferoxamine B solution. A more highly concentrated crude deferoxamine B solution generally requires less resin than does a more dilute solution The deferoxamine B adsorbs onto the resin and the aqueous solution depleted of deferoxamine B is either allowed to drain from the bed or is driven from the bed with a solution of the inorganic salt. Partially purified deferoxamine B is then recovered from the adsorption resin by eluting with a mixture of water and a water-soluble organic solvent such as methanol, ethanol, acetonitrile or tetrahydrofuran, most preferably acetonitrile. Generally, the proportion of organic solvent in the mixture should be from about 1% to about 70% (v/v), preferably about 1% to about 50% (v/v), depending on the resin. In particular, an 88:12:3 water:acetonitrile:methanol mixture is a very good solvent mixture for eluting deferoxamine B from Amberlite® XAD 1180 resin.

Gradient elution may also be advantageously used to elute deferoxamine B from any of the suitable resins. One such generally applicable gradient method involves eluting first with salt water, then with water containing an organic elution solvent. Eluting first with water, then with either a water-acetonitrile or water-methanol mixture, optionally followed by elution with a water-ethanol or water-acetone, gives good results. A particularly preferred gradient method for eluting deferoxamine B from Amberlite® XAD 1180 resin is to elute first with salt water, then with a 90:10 mixture of water-acetonitrile, and then gradually increasing the acetonitrile content to an 80:20 water-acetonitrile mixture.

Whether gradient or non-gradient elution is used, deferoxamine B will be collected from the main column dissolved in aqueous organic eluent contained in one or more fractions cut from the eluent stream. The deferoxamine B-containing eluent may optionally be decolorized such as by treatment with activated carbon or a cationic exchange resin like Amberlite® IRC 50, Duolite® C467 and Lewatit® CNP 80 according to methods known in the art. If the deferoxamine B is collected in three or more fractions—an early eluting fraction, one or more middle eluting fractions, and a late eluting fraction—then the middle fraction(s) containing deferoxamine B will typically be colorless. Only the early eluting and late eluting fractions are likely to have coloration. Accordingly, the desirability of a decolorizing treatment will depend on how the fractions are cut. If both early eluting and late eluting fractions are collected and combined with the middle fraction(s), it is desirable to use both activated carbon and a cation exchange resin to decolorize since the early-eluting and late-eluting fractions respond differently to different decolorizing methods.

Precipitation of Deferoxamine B Free Base

In the second stage of the inventive process, deferoxamine B free base is precipitated out of the eluent from the adsorption resin. Although the deferoxamine B concentration in the eluent may vary greatly depending upon the solvent mixture(s) used to elute deferoxamine B from the resin, it is not necessary to evaporate the eluent to dryness in order to establish an appropriate concentration and solvent composition for precipitating the base. Evaporation of the eluent to dryness is, in fact, disadvantageous because of the instability of the hydroxamate groups of deferoxamine B toward high solution concentration and applied heat. Rather, the eluent may be prepared for precipitation of the free base in high yield and high purity by the following the procedure.

If the deferoxamine B concentration of the eluent is lower than about 50 g $L^{-1}$, the eluent should be evaporated under mild conditions to a deferoxamine B concentration of about 50 g $L^{-1}$ to about 150 g $L^{-1}$, preferably about 80 g $L^{-1}$ to about 100 g $L^{-1}$ and most preferably about 90 g $L^{-1}$. The preferred organic elution solvents listed above are lower boiling than water and in some cases azeotrope with a minor amount of water, so the proportion of water in the solvent mixture increases upon concentration. The concentrated eluent is then diluted with acetonitrile in an amount of from about 0.5 to about 1.5 times the volume of the concentrated eluent. Addition of acetonitrile at this stage was found to prevent precipitation of deferoxamine B hydrochloride (or sulfate, as the case may be depending upon the inorganic salt used).

The concentration-adjusted eluent containing deferoxamine B in water and acetonitrile (and optionally another organic elution solvent) is then pH-adjusted to between about 8.6 and 10.5, more preferably between about 9.4 and about 10.0 pH. The pH can be adjusted using either a basic ion exchange resin or by addition of an aqueous alkaline solution or both. Suitable basic ion exchange resins include Amberlite® resins of the IRA series and Diaion® resins of the WK series, the most preferred being Amberlite® IRA 67 in OH⁻ form. Suitable alkaline solutions are solutions of NaOH, KOH, ammonia or an amine, the most preferred being concentrated aqueous ammonia.

In an especially preferred pH-adjustment technique, the pH of the concentration-adjusted eluent is first tested. If it is below pH 8.0, the pH is adjusted to between about 8.0 and 9.3 with a basic ion exchange resin such as Amberlite® IRA 67 in OH⁻ form. The resin is then separated and aqueous ammonia is added until the concentration-adjusted eluent reaches a pH of between about 9.4 and 10.0.

After pH-adjustment, crystallization of the deferoxamine B free base is induced by addition of a deferoxamine B free base anti-solvent such as acetonitrile, ethanol, methanol, or acetone. Preferred deferoxamine B free base anti-solvents are acetonitrile and acetonitrile-acetone mixtures. As used herein, the term "anti-solvent" means a liquid in which a compound is poorly soluble. Thus the term anti-solvent relates to the solubility of a particular compound in that liquid. The present invention uses two classes of anti-solvent: deferoxamine B free base anti-solvents and deferoxamine B mesylate anti-solvents.

The rate of addition of deferoxamine B free base anti-solvent to the pH-adjusted eluent is not critical, but a slower addition rate tends to produce larger crystals and a purer crystalline deferoxamine B free base. On a production scale, a practical rate of addition is about 0.5 to about 2 times the volume of pH-adjusted eluent per hour, though increased crystal size and higher purity may be realized with a slower addition rate. The total amount of added deferoxamine B free base anti-solvent is preferably about 1.5 to 10 times, more preferably about 2 to 8 times and most preferably about 2.5 to 5 times the volume of the pH-adjusted eluent. The temperature of the solution may be maintained at anywhere from about −20° C. to about 40° C. during the crystallization, although preferably the temperature is maintained at between about 0° C. and about 20° C.

After crystallization is complete, the deferoxamine B free base crystals may be isolated by any conventional means, such as filtration or decantation. Optionally, the crystals of the free base may be further purified by recrystallization. Acetonitrile-water mixtures are also good solvent systems for recrystallization.

Crystallization of Deferoxamine B Mesylate

In the third stage of the inventive process, the crystallized free base is suspended in a mixed solvent. Methanesulfonic acid is then added to the suspension which causes the deferoxamine B free base to go into solution. After complete dissolution of the deferoxamine B free base, addition of methanesulfonic acid is continued until the solution reaches a pH of about 3 to about 6, more preferably about 3.5–4.5. Deferoxamine B mesylate is then allowed to precipitate.

Suitable mixed solvents for suspending the deferoxamine B free base are mixtures of a deferoxamine B mesylate solvent, either water or methanol, and a deferoxamine B mesylate anti-solvent. Deferoxamine B mesylate anti-solvents include $C_1$–$C_7$ aliphatic alcohols, acetone, methyl formate, methyl acetate, ethyl acetate, hexane, toluene, tetrahydrofuran and acetonitrile. The polar, solvent component of the mixed solvent, i.e. the methanol or the water, is preferably mixed in a ratio of about 1:1 to about 1:10 with the anti-solvent component, more preferably in a ratio of about 1:5. Preferred mixed solvents are water-ethanol mixtures, water-acetonitrile mixtures, methanol-ethanol mixtures and methanol-acetonitrile mixtures, the most preferred being 1:5 water-ethanol mixtures and 1:3 methanol-ethanol mixtures. The volume of mixed solvent that should be used to suspend the free base is from about 5 to about 20 L per kilogram of deferoxamine B free base, more preferably from about 7 to about 15 L per kilogram.

After forming the suspension, methanesulfonic acid is added to the suspension. The amount of methanesulfonic acid that is required can be approximated by calculating the amount required to provide one equivalent of the acid to the base. Alternatively, the amount of methanesulfonic acid necessary to provide one equivalent may be accurately gauged by observing the amount of undissolved free base that remains suspended during addition of the acid. The methanesulfonic acid should be added slowly for this purpose since the rate at which the suspended base can react with the acid is rate limited by the surface area of the crystals. After the all of the deferoxamine B free base has dissolved, the pH of the solution should be monitored, while additional methanesulfonic acid is added to bring the pH of the solution to between about 3 and about 6, preferably about 3.5–4.5. After the desired pH is reached, deferoxamine B mesylate crystals are allowed to precipitate.

To accelerate precipitation, the solution may be cooled to about −20 to about 10° C. In addition, precipitation may be accelerated by adding more deferoxamine B mesylate anti-solvent to the mixture, i.e. by adding a $C_1$–$C_7$ aliphatic alcohol, acetone, methyl formate, methyl acetate, ethyl acetate, hexane, toluene, tetrahydrofuran or acetonitrile. After precipitation is complete deferoxamine B mesylate is isolated by conventional means such as filtration or decantation.

Having thus described the inventive process with reference to its preferred embodiments, the invention will now be further illustrated by the examples which follow.

EXAMPLES

General

HPLC Conditions (Reverse phase): column: $C_{18}$, particle size 10μ, length 250 mm, diameter 4.6 mm; mobile phase: 5.5% THF/water, 0.13% $(NH_4)H_2PO_4$ (w/v), 0.04% sodium edetate (w/v); flow rate: 2 ml min.$^{-1}$; detection: UV λ=220 nm.

Example 1

Crude deferoxamine B hydrochloride (7.88 kg) containing 5.30 kg deferoxamine B was dissolved in water (362 L). The aqueous solution was then passed through an equal volume of Diaion® SP 207 adsorption resin (Mitsubishi Chemical Corp.) in a 10 liter chromatographic column at a flow rate of 14 L h$^{-1}$. The eluent contained 5.04 kg deferoxamine. Ammonium chloride was then added in an amount of 5 g L$^{-1}$ to the eluent with stirring until the ammonium chloride completely dissolved. The solution was then loaded onto a column containing Amberlite® XAD 1180 adsorption resin (132 L) (Rohm & Haas) and driven into the bed with salt water. The column was eluted with 10% acetonitrile-water and then 20% acetonitrile-water at a flow rate of 14 L h$^{-1}$. The eluent was collected in fractions. The main fraction yielded deferoxamine hydrochloride solution containing 4.53 kg of deferoxamine B. The main fraction was then decolorized over activated carbon (45 g) and Duolite® C 467 (Rohm and Haas) ion exchange resin in H$^+$ form yielding deferoxamine hydrochloride solution containing 4.03 kg of deferoxamine B.

The decolorized eluent was evaporated to a deferoxamine B concentration of 90 g L$^{-1}$. A volume of acetonitrile equal to that of the concentrated eluent was then added and the basicity was adjusted by addition of Amberlite® IRA 67 (Rohm and Haas) in OH$^{-1}$ form to a pH between 8.014 9.3. After pH-adjustment with the anion exchange resin, the pH was raised to between 9.4 and 10.0 with aqueous ammonia. Deferoxamine free base was then precipitated by adding two volumes of acetonitrile to the solution and cooling to −5° C. Crystallization was complete after several hours. The crystals of deferoxamine free base were isolated by filtration and then suspended in 1:1 acetonitrile-water, filtered again, washed with acetonitrile and dried to yield 3.81 kg of deferoxamine free base. HPLC chromatography showed that the free base was 97% pure. Following the USP chemical test <221> for determining chloride content, the precipitated deferoxamine B free base was found to have a chloride content of less than 60 ppm. *USP/NF*24/19, pp. 1857–1858 (1999)

The deferoxamine free base was suspended in a 14:3 mixture of ethanol and water (42.5 L). Dilute methanesulfonic acid was slowly added to the suspension until the free base dissolved and the solution attained a pH of between 3.7 and 5. Ethanol (200 L) was added to the solution to precipitate the mesylate salt and the resulting suspension was cooled to −10° C. and maintained at −10° C. for several hours. The resulting crystals were isolated by filtration, washed with ethanol (50 L) and dried under vacuum to yield 3.4 kg of deferoxamine mesylate. HPLC chromatography showed that the mesylate contained 1.84 weight % impurities. The moisture content as determined by Karl-Fischer Analysis was 0.2 mole %. *USP/NF* 24/19, pp. 2003–2004 (1999). Coloration was better than Y5 as measured according to the European Pharmacopeia criteria for grading coloration.

Example 2

Crude deferoxamine B hydrochloride (707 g) containing 587 g deferoxamine B was dissolved in water (10 L). The aqueous solution was passed through a chromatography column containing Diaion® SP 207 adsorption resin (1 L) at a flow rate of 0.35 L h$^{-1}$. The eluent from the column was found to contain 562 g of deferoxamine B. The eluent was then loaded onto a bed of Amberlite® XAD 1180 adsorption resin (7.2 L) in a chromatography column. The bed was eluted at a flow rate of 0.7 L h$^{-1}$, first with 5.6 L of a 10 g L$^{-1}$ solution of ammonium chloride in water and then with a 1:4 methanol-water mixture. Deferoxamine B (432 g) was collected in a single fraction. This fraction was decolorized by stirring over activated charcoal (40 g) and filtered. The decolorized eluent was evaporated to a deferoxamine B concentration of 60 g L$^{-1}$.

An equal volume of acetonitrile was then added. Concentrated aqueous ammonia was then added until the solution attained a pH of 9.8. Then, four volumes of acetonitrile were added to precipitate the deferoxamine B free base. The resulting suspension was cooled to −4° C. and maintained at reduced temperature for 24 h, after which time the crystals were isolated by filtration. The isolated crystals were then washed by three repetitions of suspending in 1:1 water-acetonitrile and filtering. The crystals were then dried at 40° C. at ambient pressure to yield the deferoxamine B free base (341 g) in 95.2% purity (w/w) as determined by HPLC and with a chloride content of less than 60 ppm.

The deferoxamine B base was then suspended in a mixture of ethanol (3.1 L) and water (0.46 L). Methanesulfonic acid was slowly added until the deferoxamine B base dissolved and the solution reached a pH of 3.5. Another 30 L of ethanol was added to the solution to precipitate deferoxamine B mesylate. The resulting suspension was then cooled to between −5° C. and 0° C. and maintained at reduced temperature for 24 h. The crystals were isolated by filtration, washed with ethanol and dried under vacuum to yield deferoxamine B mesylate (299 g) with a purity of 98% (w/w) as determined by HPLC analysis.

Example 3

Crude deferoxamine B hydrochloride (760 g) containing 530 g of deferoxamine B was dissolved in 1:1 acetonitrile-water ( 14 L) at 40° C. The resulting solution was then filtered and pH-adjusted to 9.9 by addition of concentration aqueous ammonia. Acetonitrile (49 L) was then added to precipitate the deferoxamine B free base. The resulting suspension was then cooled to 17° C. and maintained at reduced temperature for four hours. The precipitate was isolated by filtration, washed with acetonitrile and dried under reduced pressure to yield deferoxamine B free base (403 g). The base was then suspended in water (20 L) and hydrochloric acid was slowly added until the base dissolved and the resulting solution reached a pH of between 5.0 and 5.5.

The solution was loaded onto a bed of Amberlite® XAD 1180 adsorption resin (7.2 L) in a chromatography column and eluted with 25% acetonitrile-water. The deferoxamine B (320 g) was obtained in a single fraction. The deferoxamine B-containing eluent was decolorized over activated charcoal (10 g). After filtration, the decolorized eluent containing 305 g of deferoxamine B was concentrated to about 110 g L$^{-1}$. An equal volume of acetonitrile then was added to the solution. The pH of the solution was then adjusted to between 8.6 and 9.0 by adding Amberlite® IRA 67 anion exchange resin in OH$^{-1}$ form. Aqueous ammonia was added to the solution to precipitate deferoxamine B free base. The addition was continued until the suspension reached pH 9.8. The suspension was then cooled to −4° C. and maintained at reduced temperature for several hours. Crystals were then isolated by filtration and suspended in a 1:1 mixture of acetonitrile-water, filtered again and then dried under reduced pressure. The dried deferoxamine B free base was then powdered before being used to prepare the mesylate salt as described in Example 1, last paragraph. The powdered free base was found to be 97.8% (w/w) pure by HPLC analysis. The mesylate salt obtained using this material contained 0.96% impurity (w/w) by HPLC analysis and had a chloride content of less than 60 ppm.

Example 4

Deferoxamine B mesylate was isolated from crude deferoxamine B according to the process of Example 2, except that deferoxamine B hydrochloride was eluted from the bed of Amberlite® XAD 1180 adsorption resin using 15% ethanol-water followed by 25% THF-water. The deferoxamine mesylate (238 g) so obtained was found to have an impurity content of 1.73% (w/w) by HPLC analysis.

Example 5

Crude deferoxamine B hydrochloride was chromatographed according to the procedure described in Example 1. After the deferoxamine B-containing eluent was concentrated to 90 g L$^{-1}$ and decolorized as described in Example 1, the decolorized eluent was divided into three equal portions containing 40 g of deferoxamine B each. Each portion was diluted with an anti-solvent. One portion was diluted with an equal volume of methanol, another with an equal volume of ethanol and the other with an equal volume of acetone. The pH of each of the portions was then adjusted to between 8.6 and 10.1 with aqueous ammonia causing deferoxamine B free base to come out of solution. Precipitation was completed by addition of triple the portion volume of a 1:1 acetonitrile-anti-solvent mixture to each portion, i.e. either acetonitrile-methanol, acetonitrile-ethanol or acetonitrile-acetone. The suspensions were then cooled to −20 to −5° C. and deferoxamine B free base was isolated from each suspension by filtration. The crystals were then washed as described in Example 1. Following the procedure for converting the free base to the mesylate in Example 1, deferoxamine B mesylate is obtained in amounts of from 24–28 g. starting from 40 g of crude deferoxamine B. The impurity content of the so-obtained deferoxamine B mesylate was between 1:1 and 1.5% (w/w).

Example 6

The process of Example 2 was followed, except that the crude deferoxamine B contained sulfate anion and the Amberlite® XAD 1180 resin was washed with aqueous ammonium sulfate instead of aqueous ammonium chloride and then eluted with 10% acetonitrile-water instead of a 1:4 methanol-water mixture. The so-obtained deferoxamine B mesylate salt (261 g) had an impurity content of 1.4% (w/w) measured by HPLC.

Example 7

A suspension of deferoxamine B free base was prepared according to the procedure of Example 2 and cooled as described to 4° C. A one tenth portion of the suspension containing 34.1 g of deferoxamine B free base was heated to 36° C. and stirred at elevated temperature for 1 hour and then filtered to recover the free base. The recovered crystals were then dried and converted to the deferoxamine B mesylate as described in Example 2. The product (27 g) had an impurity content of 1.4% (w/w) as determined by HPLC analysis.

Example 8

The process of Example 2, paragraphs 1 and 2, was followed, except that a portion of the eluent containing 43.2 g of deferoxamine B was not decolorized. The free base was twice precipitated from this portion of the eluent. The deferoxamine B was first precipitated as described in Example 2, paragraph 2. Then the once-precipitated deferoxamine B base was suspended in a 1:1 acetonitrile-water mixture at a concentration of 40–50 g $L^{-1}$. One molar hydrochloric acid was then slowly added to the suspension until the deferoxamine B dissolved, The deferoxamine B free base was then re-precipitated from the solution by following the procedure of Example 2, paragraph 2, and was transformed into the mesylate salt as described in Example 2, paragraph 3, to yield 27 g of deferoxamine B mesylate. Product coloration was indistinguishable from that of the product of Example 2. The impurity content as measured by HPLC is 1.4% (w/w).

Example 9

Following the procedure of Example 1, crude deferoxamine B was chromatographed and the eluent containing deferoxamine B (45.3 g) was decolorized. The decolorized solution was concentrated to 90 g $L^{-1}$ and passed through a bed of Diaion® SP 207 adsorption resin. Proceeding with the procedure for precipitating the free base and converting it to the mesylate salt as described in the second and third paragraphs of Example 1, as much as 31.5 g of the mesylate can be obtained and with only 1.46% (w/w) impurity according to HPLC analysis.

Example 10

The procedure of Example 1 was followed except that 200 L of acetonitrile was substituted for 200 L of ethanol to induce precipitation of deferoxamine mesylate. Deferoxamine B mesylate was obtained in 94.7% yield.

Following the procedure of Example 1, but substituting propanol, butanol, amyl alcohol, hexanol and heptanol for ethanol to induce precipitation of the deferoxamine B mesylate, the mesylate is obtained in yields ranging from 83.1 to 89.1%.

Substituting ethyl formate, ethyl acetate, butyl acetate, hexane and THF for ethanol in the procedure of Example 1, deferoxamine B mesylate is obtained in yields ranging from 88.1 to 93.1%.

In each of these variations on the Example 1 procedure, impurity was present in less than 2.5% (w/w) as determined by HPLC.

Example 11

Deferoxamine mesylate prepared according to Example 1 was recrystallized from methanol and mixtures of methanol and other solvents in yields ranging from 81.3 to 93.7%. Recrystallization was performed by dissolving deferoxamine B mesylate in 8.5 volumes of methanol at 35° C. and then adding one of the following solvents at room temperature: methanol, ethanol, propanol, butanol, ethyl formate, ethyl acetate, butyl acetate, hexane, toluene, THF or acetonitrile. The recrystallized deferoxamine B mesylate typical had 1.2–1.6% (w/w) impurity, lower than the 1.84% (w/w) impurity level of the material before recrystallization.

Having described the invention with reference to its preferred embodiments and having further illustrated the invention with specific examples, those of ordinary skill in the art may, upon reading this disclosure, apprehend modifications that could be made which do not depart from the spirit and scope of the invention. It should therefore be understood that the description and examples presented above are for illustrative purposes only and should not be read as limiting the scope of the invention as set forth in the claims, which follow.

What is claimed is:

1. A process for isolating deferoxamine B mesylate from a source material containing deferoxamine B produced by a microbiological process comprising the steps of:
   a) adsorbing deferoxamine B onto an adsorption resin by contacting the source material with the adsorption resin,
   b) obtaining an eluent containing deferoxamine B by eluting the adsorption resin having deferoxamine B adsorbed thereon with a mixture of water and a water-soluble organic elution solvent,
   c) adjusting the pH of the eluent to between about 8.6 and 10.5 with a basic ion exchange resin or an alkaline solution, or both,
   d) crystallizing deferoxamine B free base from the pH-adjusted eluent by addition of a deferoxamine B free base anti-solvent, optionally after partial concentration of the eluent to a deferoxamine B concentration of not more than 150 g $L^{-1}$,
   e) suspending the deferoxamine B free base in a mixed solvent comprising a deferoxamine B mesylate anti-solvent and a deferoxamine B mesylate solvent selected from the group consisting of water and methanol,
   f) dissolving the deferoxamine B free base in the mixed solvent by contacting the suspension with methanesulfonic acid, and
   g) precipitating deferoxamine B mesylate.

2. The process of claim 1 further comprising the preliminary step of passing the source material through a pre-column bed of adsorption resin.

3. The process of claim 1 further comprising the preliminary step of adding an inorganic salt to the source material.

4. The process of claim 3 wherein the inorganic salt is ammonium chloride or ammonium sulfate.

5. The process of claim 1 wherein the adsorption resin is eluted with a mixture of water and a water-soluble organic solvent selected from the group consisting of methanol, ethanol, acetonitrile and tetrahydrofuran.

6. The process of claim 5 wherein the water-soluble organic solvent is acetonitrile.

7. The process of claim 1 further comprising the intermediate step of decolorizing the eluent before adjusting the pH of the eluent.

8. The process of claim 1 further comprising adjusting the deferoxamine B concentration of the eluent before adjusting the pH of the eluent.

9. The process of claim 8 wherein the deferoxamine B concentration in the eluent is adjusted to from about 50 g $L^{-1}$ to about 150 g $L^{-1}$ by evaporation.

10. The process of claim 9 wherein the deferoxamine B concentration is adjusted to from about 80 g $L^{-1}$ to about 100 g $L^{-1}$.

11. The process of claim 10 wherein the deferoxamine B concentration is adjusted to about 90 g $L^{-1}$.

12. The process of claim 8 further comprising adding acetonitrile to the eluent after concentration-adjustment and before pH-adjustment.

13. The process of claim 1 wherein the pH of the eluent is adjusted to between about 9.4 and about 10.

14. The process of claim 1 where the pH of the eluent is adjusted by addition of an alkaline solution.

15. The process of claim 14 wherein the alkaline solution is a solution of NaOH, KOH, ammonia or an amine.

16. The process of claim 15 wherein the alkaline solution is aqueous ammonia.

17. The process of claim 1 wherein the pH of the eluent is adjusted using a basic ion exchange resin.

18. The process of claim 13 wherein the pH of the eluent is adjusted to between about 9.4 and about 10 by adding a basic ion exchange resin to the eluent until a pH between about 8.0 and about 9.3 is reached, separating the basic ion exchange resin and adding aqueous ammonia until a pH of between about 9.4 and 10 is reached.

19. The process of claim 1 wherein the mixed solvent in which the deferoxamine B free base is suspended comprises water and a deferoxamine B mesylate anti-solvent selected from the group consisting of $C_1$–$C_7$ aliphatic alcohols, acetone, methyl formate, methyl acetate, ethyl acetate, hexane, toluene, tetrahydrofuran and acetonitrile.

20. The process of claim 19 wherein the deferoxamine B mesylate anti-solvent is selected from the group consisting of ethanol, acetone and acetonitrile.

21. The process of claim 1 wherein the mixed solvent in which the deferoxamine B free base is suspended comprises methanol and a deferoxamine B mesylate anti-solvent selected from the group consisting of $C_1$–$C_7$ aliphatic alcohols, acetone, methyl formate, methyl acetate, ethyl acetate, hexane, toluene, tetrahydrofuran and acetonitrile.

22. The process of claim 21 wherein the deferoxamine B mesylate anti-solvent is selected from the group consisting of ethanol, acetone and acetonitrile.

23. The process of claim 1 wherein precipitation of deferoxamine B mesylate is accelerated by cooling.

24. The process of claim 1 wherein precipitation of deferoxamine B mesylate is accelerated by adding a deferoxamine B mesylate anti-solvent selected from the group consisting of $C_1$–$C_7$ aliphatic alcohols, acetone, methyl formate, methyl acetate, ethyl acetate, hexane, toluene, tetrahydrofuran and acetonitrile.

25. The process of claim 1 wherein the precipitated deferoxamine B mesylate has a chloride ion content of about 90 ppm or less.

26. The process of claim 1 wherein the precipitated deferoxamine B mesylate contains less than about 2.5 mole % other polyhydroxamates based upon the moles of deferoxamine B.

* * * * *